Figure 5A:
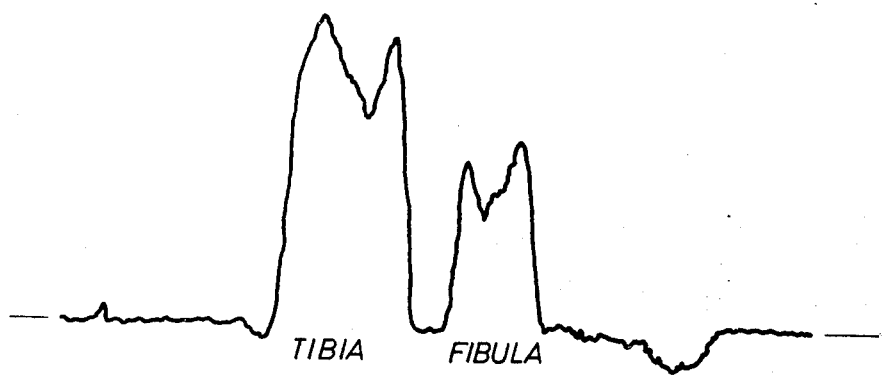

United States Patent [19]
Dissing

[11] 3,944,830
[45] Mar. 16, 1976

[54] METHOD OF AND AN APPARATUS FOR EXAMINING A SAMPLE OR A MATERIAL BY MEASURING THE ABSORPTION OF γ- OR X-RAY RADIATION

[75] Inventor: Erik Dissing, Nykoping, Sweden

[73] Assignee: Aktiebolaget Atomenergi, Stockholm, Sweden

[22] Filed: May 10, 1974

[21] Appl. No.: 469,009

[30] Foreign Application Priority Data
May 11, 1973 Sweden............................ 7306721

[52] U.S. Cl.............................. 250/358 R; 250/308
[51] Int. Cl.².......................................... G01N 23/02
[58] Field of Search ............ 250/308, 358, 359, 360

[56] References Cited
UNITED STATES PATENTS

| | | | |
|---|---|---|---|
| 2,884,535 | 4/1959 | Swift, Jr.............................. | 250/308 |
| 3,432,657 | 3/1969 | Slavin ................................. | 250/359 |
| 3,529,151 | 9/1970 | Carr-Brion....................... | 250/359 X |
| 3,778,614 | 12/1973 | Hounsfield...................... | 250/360 X |

Primary Examiner—Archie R. Borchelt
Attorney, Agent, or Firm—Toren, McGeady and Stanger

[57] ABSTRACT

A method of and an apparatus for human bone density determination in vivo. γ- or x-ray radiation of two different photon energies is scanned across the human body part to be examined. For the two photon energies, the logarithms of the intensities of the radiation transmitted through the human body part are determined simultaneously. The logarithm values obtained are processed on line such that the ratio of these values is changed by a predetermined factor. The processed values are subtracted from each other to produce a simultaneous output value which is integrated to give an examination result proportional to the bone tissue content expressed as weight per length unit in a direction perpendicular to the scanning direction while being independent of the surrounding soft tissue.

18 Claims, 10 Drawing Figures

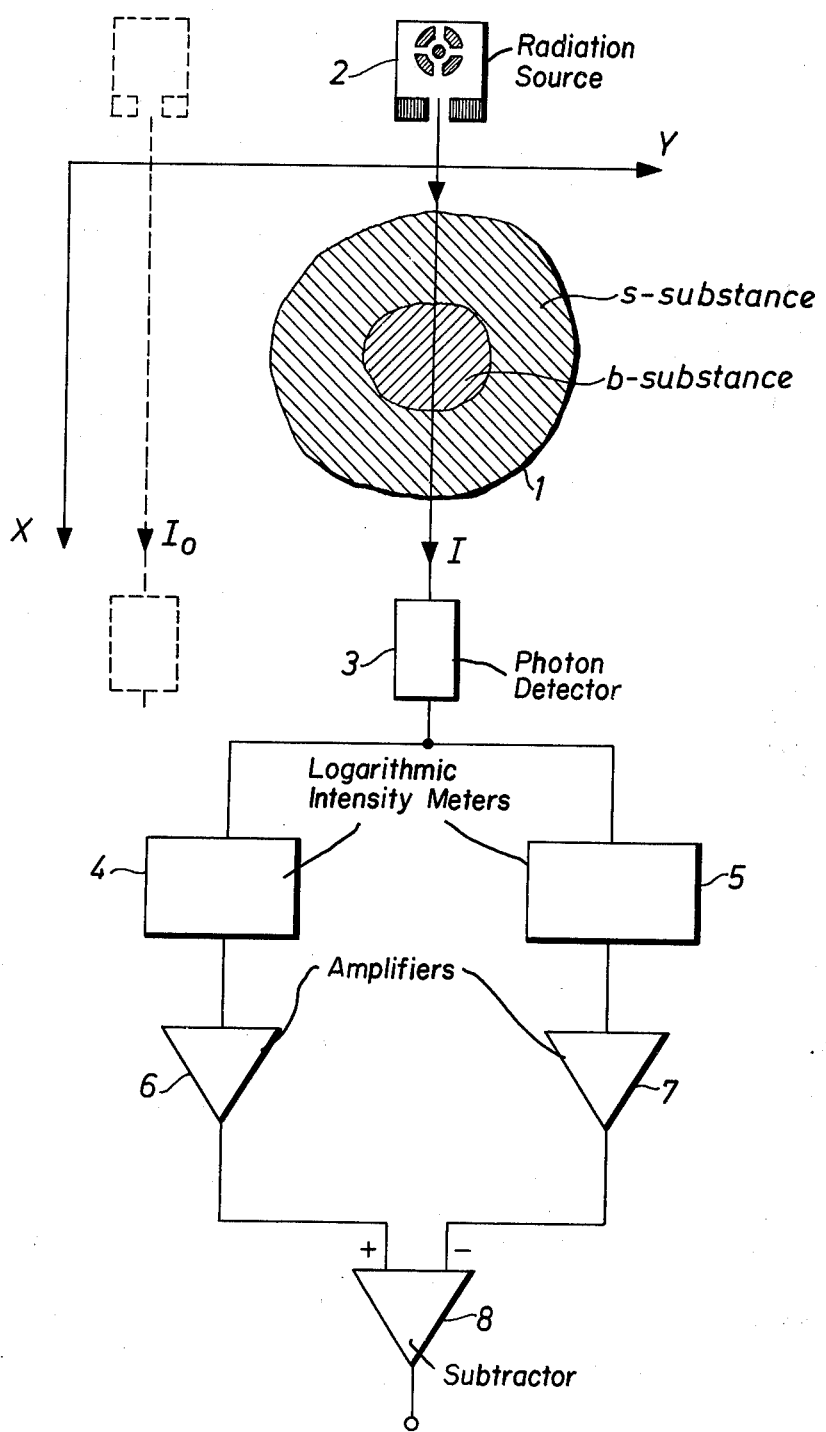

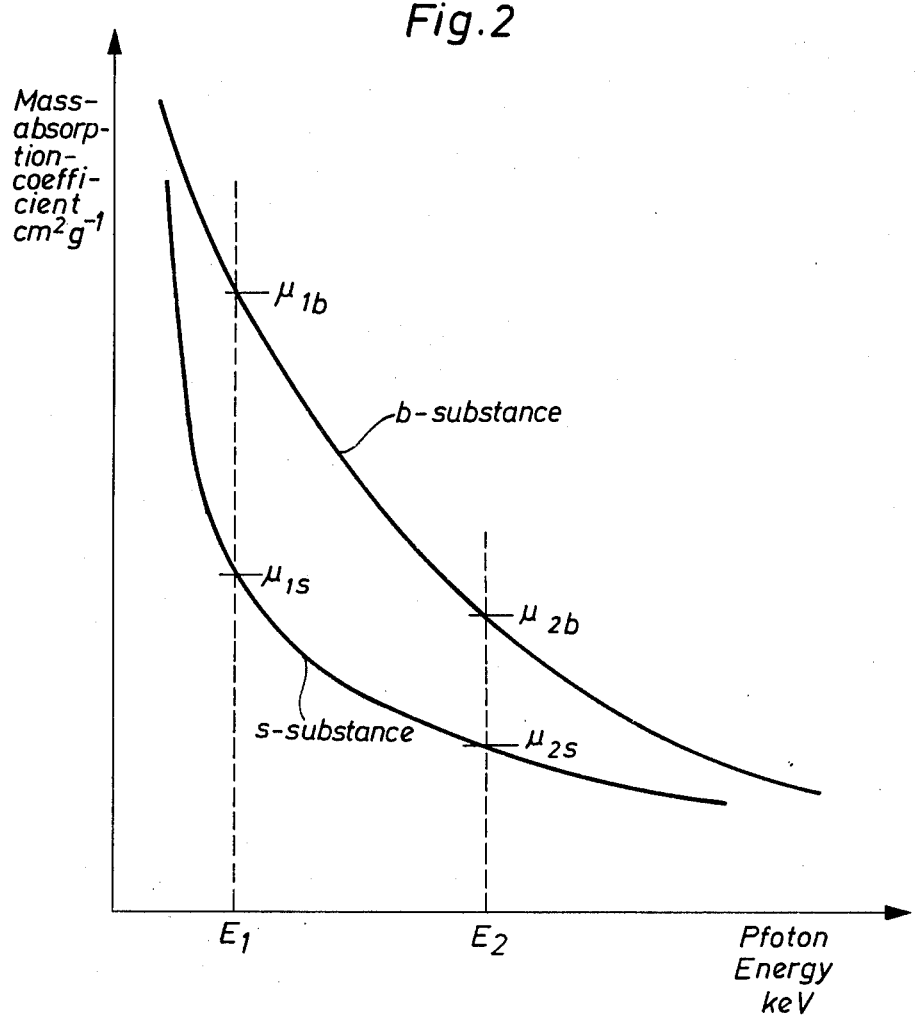

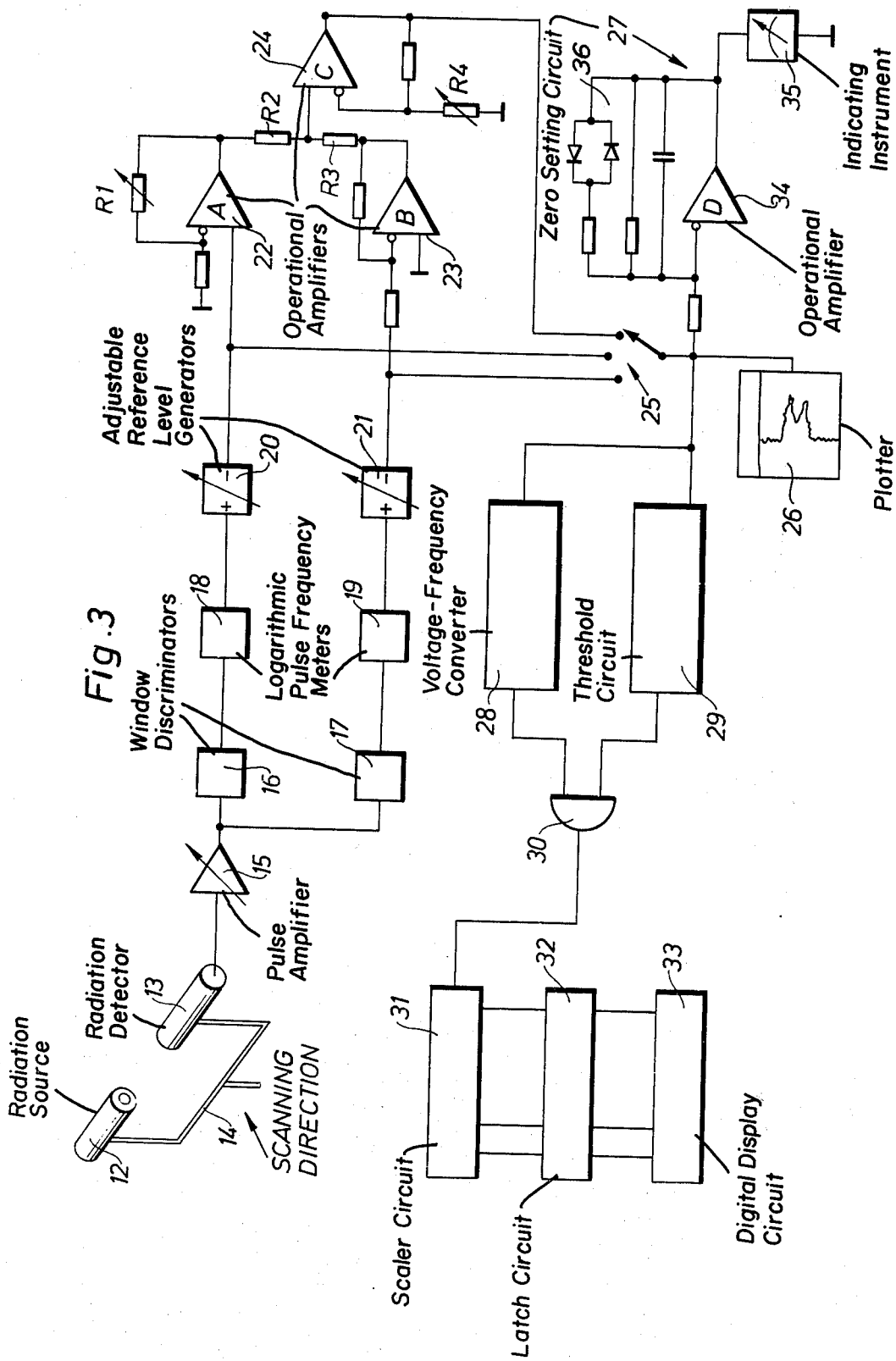

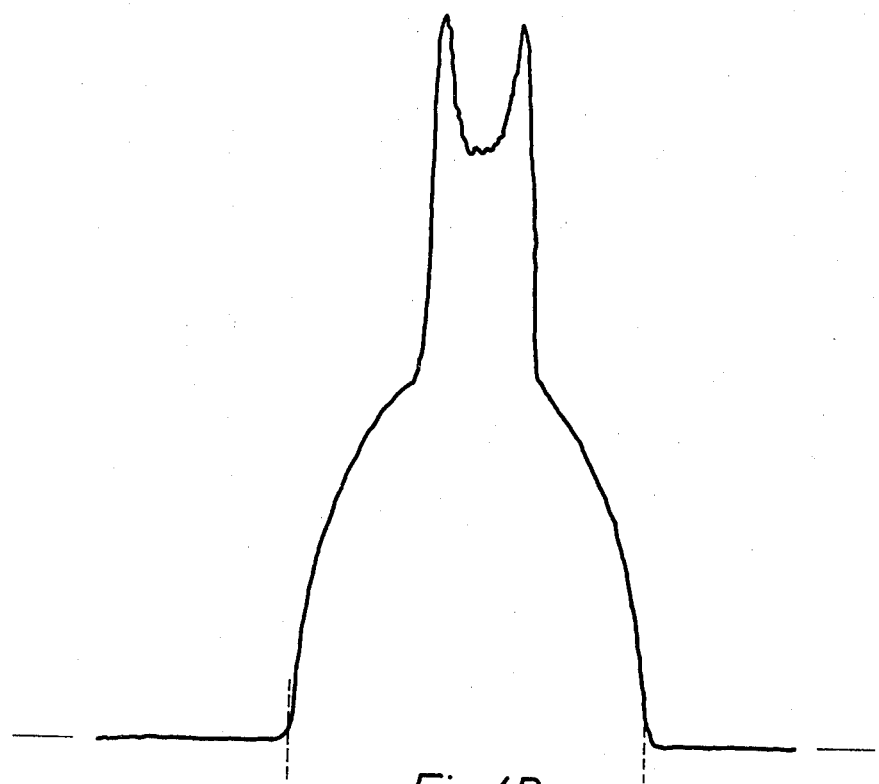
Fig. 4C
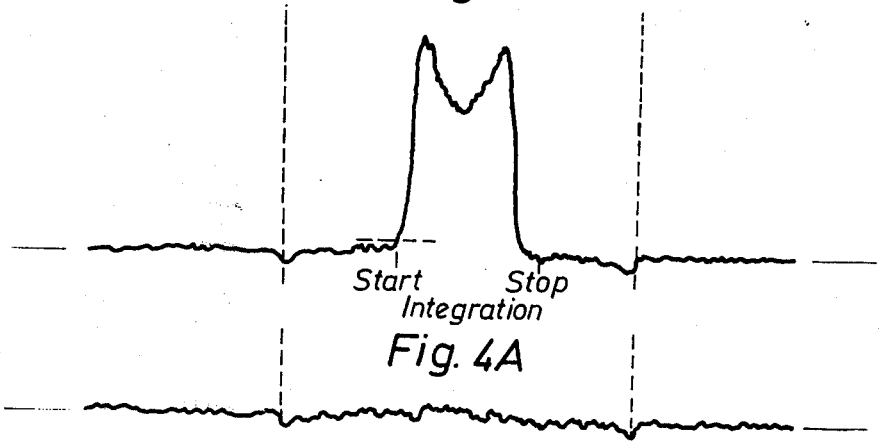
Fig. 4B
Start — Stop
Integration
Fig. 4A

TIBIA    FIBULA

ULNA    RADIUS

OSSA   MANUS

METHOD OF AND AN APPARATUS FOR EXAMINING A SAMPLE OR A MATERIAL BY MEASURING THE ABSORPTION OF Γ- OR X-RAY RADIATION

The present invention relates to the examination of a sample or a material, preferably the examination of the structure of biological tissue, which includes at least two different substances, by measuring the absorption of γ- or x-ray radiation transmitted through the sample. The invention is particularly applicable to the determination in vivo of the mineral content in the human body skeleton.

It is known to use in bone density determination in vivo a method based upon the use of a radioactive radiation source emitting photons of one specific energy. When using this method, the so-called single isotope method, the body part to be exposed to radiation is submerged in a liquid, for instance water, having substantially the same linear absorption coefficient as has the soft tissue surrounding the bone, the mineral content of which is to be determined. In this way it is possible to a certain extent to compensate for the radiation absorption in said soft tissue. However, submerging the body part in a liquid means disadvantages which reduce the applicability of the method.

Therefore, the so-called double isotope method has been developed, which means that the test results of absorption measurements using two different isotopes of different photon energies are combined and calculated. In this way the influence of soft tissue can be eliminated without any use of liquid surrounding the body part examined. The specific content of the two substances is obtained by calculating the separate test results of the two isotopes. The calculation, generally being comparatively extensive, is suitably carried out by means of a desk calculator.

Consequently, the object of the present invention is to provide a method of and an apparatus for examination of the type of sample mentioned above while using radiation of at least two different photon energies, whereby the influence of one of the substances of the sample on the examination result is simultaneously and automatically eliminated, such that the examination result directly gives the content of the other substance or substances.

The above-mentioned object is achieved in that the method and the apparatus according to the invention show the features defined in the appended claims.

Thus, the method according to the invention comprises transmitting radiation including photons of at least two different energies through the sample; simultaneously for a first and a second of two predetermined photon energies determining the logarithm of the radiation intensity of the radiation passed through the sample; processing the logarithmic value obtained such that the ratio of said values is changed by a predetermined factor; and subtracting the logarithmic values thus processed from each other in order to obtain a simultaneous examination value, said predetermined factor being chosen such that the influence of one of the substances on the magnitude of the examination value is eliminated. The ratio between the logarithm value at the first photon energy and the logarith value at the second photon energy is changed with a factor being substantially equal to the ratio between the mass absorption coefficient of said one substance at the second photon energy and the mass absorption coefficient of said one substance at the first photon energy. Suitably, the sample is examined by scanning the radiation transmitted through the sample in a first direction while continuously and simultaneously producing the examination value. Advantageously, the examination value is simultaneously recorded to produce a curve showing for instance a bone density profile. It is also advantageous during the scanning to integrate the portion of the examination value produced which is a function of the influence of said other substance or substances on the radiation, whereby a value is obtained that is proportional to the content of the sample of said other substance or substances in terms of weight per length unit in a direction perpendicular to said first direction.

The apparatus according to the invention comprises a radioactive radiation source emitting γ- or x-ray radiation having photons of at least two different energies and detector means for determining the intensity of radiation transmitted from said radiation source and falling on the detector means and is essentially characterized in that said detector means are arranged to produce simultaneously a first signal having a quantity proportional to the logarithm of the radiation intensity at a first photon energy and a second signal having a quantity proportional to the logarithm of the radiation intensity at a second photon energy, in that means are arranged for processing said first and second signal such that the ratio between said quantities is changed by a certain factor, and in that means are arranged to produce an output signal having a quantity proportional to the difference between said changed quantities of the processed signals, said first-mentioned means being arranged to change said ratio such that said quantity of the output signal is substantially independent of the influence of said one substance on the radiation. The radiation source and the detector means are suitably arranged such that the radiation beam can be scanned across the sample while simultaneously producing the output signal. Advantageously, recording means for recording said quantity of the output signal are provided. Also, it is advantageous to provide integrating means for integrating a signal being proportional to said quantity of said output signal.

The invention will now be described in more detail while referring to the accompanying drawings, in which FIG. 1 schematically shows the basic principal of the invention, FIG. 2 exemplifies the dependence of the mass absorption coefficient $\mu$ on the photon energy E of the absorbed radiation for different substances, FIG. 3 shows a block diagram of a preferred embodiment of an apparatus according to the invention, FIGS. 4A, B, C and 5A, B, C show registrations of measuring results obtained by an apparatus constructed in accordance with FIG. 3, and FIG. 6 exemplifies how scanning can be accomplished.

Referring to FIG. 1, a sample 1 is examined, the sample being shown in cross-section and including a substance $b$, for instance bone tissue, and a substance $s$, for instance soft tissue, by means of a radioactive radiation source 2 and detector means including a photon detector 3, two logarithmic intensity meters or ratemeters 4 and 5, two amplifiers 6 and 7, and a subtractor 8. The radiation source 2 emits photons of two different energies $E_1$ and $E_2$, the mass absorption coefficients of the two substances being $\mu_{1b}$ and $\mu_{1s}$ at photon energy $E_1$, and $\mu_{2b}$ and $\mu_{2s}$ at photon energy $E_2$, as shown in FIG. 2.

The logarithmic intensity meter 4 is arranged to produce a signal proportional to the logarithm of the incident radiation intensity $I_1$ at energy $E_1$ at photon detector 3 and the logarithmic intensity meter 5 is arranged to produce a signal proportional to the logarithm of the simultaneously incident radiation intensity $I_2$ at energy $E_2$ at detector 3. Signal amplifiers 6 and 7 have amplification factors $F_1$ and $F_2$, respectively. Radiation source 2 and photon detector 3 are displaceable relative to sample 1 in the y-marked direction, whereby the radiation propagating in the x-marked direction can be swept or scanned across the sample.

If the radiation intensities at energies $E_1$ and $E_2$ when passing free through the air (indicated by broken lines in FIG. 1) are denoted $I_{01}$ and $I_{02}$, respectively, the following conditions as to the attenuation in the sample will be valid with some approximation, as is well known:

$$\ln I_1 = \ln I_{01} - K \mu_{1s} \rho_s x_s - K \mu_{1b} \rho_b x_b \tag{1}$$

and $$\ln I_2 = \ln I_{02} - K \mu_{2s} \rho_s x_s - K \mu_{2b} \rho_b x_b \tag{2}$$

$\rho_s$ and $\rho_b$ being the densities of the s-substance and the b-substance, respectively, $x_s$ and $x_b$ being the distances of passage of the radiation through s-substance and b-substance, respectively, $K$ being a constant, and $\mu_{1s}$, $\mu_{1b}$, $\mu_{2s}$ and $\mu_{2b}$ being the mass absorption coefficients mentioned earlier.

Thus, the output signal $U_{out}$ of subtractor 8 will be $$F_1 \ln I_{01} - F_2 \ln I_{02} - K \,_s\mu_{1s} F_1 \left(1 - \frac{F_2}{F_1} \cdot \frac{\mu_{2s}}{\mu_{1s}}\right) x_s - K \,_b\mu_{1b} F_1$$

$$\left(1 - \frac{F_2}{F_1} \cdot \frac{\mu_{2b}}{\mu_{1b}}\right) X_b \tag{3}$$

Provided that $$\frac{F_2}{F_1} = \frac{\mu_{1s}}{\mu_{2s}}$$

the output signal will be $$F_1 \left(\ln I_{01} - \frac{\mu_{1s}}{\mu_{2s}} \ln I_{02}\right) - K F_1 \mu_{1b} \left(1 - \frac{\mu_{1s}}{\mu_{2s}} \cdot \frac{\mu_{2b}}{\mu_{1b}} \rho_b X_b\right) \tag{4}$$

that is the magnitude of the output signal will be independent of $x_s$. In other words, the detector means will be "blind" as to the s-substance and produce an output signal which apart from fluctuations due to the random photon detection only varies responsive to the content of b-substance.

For the purpose of simplification, suitably, a signal corresponding to $$F_1 \left(\ln I_{01} - \frac{\mu_{1s}}{\mu_{2s}} \ln I_{02}\right),$$

is subtracted from the output signal according to (4), whereby the output signal will be $$U_{out} = K_1 \mu_{1b} \left(1 - \frac{\mu_{1s}}{\mu_{2s}} \cdot \frac{\mu_{2b}}{\mu_{1b}}\right) \rho_b X_b \tag{5}$$

The above-mentioned simplification, which can easily be obtained by subtracting a reference generator signal from said output signal according to (4) or by subtracting or adding said signal in a suitable way after each of or both of amplifiers 6 and 7, means that the output signal according to (5) is in direct proportional to the contents of b-substance of the sample.

The above-mentioned simplified equation (5) as to the output signal is obtained if each of intensity meters 4 and 5 is arranged to produce a signal proportional to the logarithm of the ratio between the intensity of radiation when passing free through the air and the intensity of radiation when passing through the sample, that is, proportional to ln ($I_0/I$), and naturally if the radiation intensifies $I_{01}$ and $I_{02}$ are chosen such that $$\ln I_{01} - \frac{\mu_{1s}}{\mu_{2s}} \ln I_{02} = 0$$

If the radiation is scanned across the sample in the way mentioned above and the output signal according to (5) is integrated simultaneously, the following equation as to the resulting signal is obtained:

$$\int U_{out}(t) dt = K_1 \cdot \mu_{1b} \cdot \left(1 - \frac{\mu_{1s}}{\mu_{2s}} \cdot \frac{\mu_{2b}}{\mu_{1b}}\right) \cdot \rho_b \cdot \int x_b(t) dt \tag{6}$$

If the scanning speed $dy/dt$ is constant and equals $v$ and the effective area of the b-substance in the scanning plane is $A$ we obtain $$\int U_{out}(t) dt = K_1 \cdot \mu_{1b} \left(1 - \frac{\mu_{1s}}{\mu_{2s}} \cdot \frac{\mu_{2b}}{\mu_{1b}}\right) \cdot \rho_b \cdot \frac{A}{v} \tag{7}$$

and $$\rho_b \cdot A = K_2 \frac{1}{\mu_{1b} \left(1 - \frac{\mu_{1s}}{\mu_{2s}} \cdot \frac{\mu_{2b}}{\mu_{1b}}\right)} \int U_{out}(t) dt \tag{8}$$

In other words the content of b-substance in the scanning plane expressed as grams per length unit (perpendicular to the scanning plane) is proportional to, signal obtained after integration. The factor of proportionality can be determined by calculating $K_2$ and the $\mu$-coefficient expression, the latter from out of a complete knowledge of the atomic composition of the two substances involved. However, since linear conditions can be assumed, the factor of proportionality can be easily determined or the apparatus normalized by means of a dummy made from the two substances and having a known content of b-substance.

Figure 6:
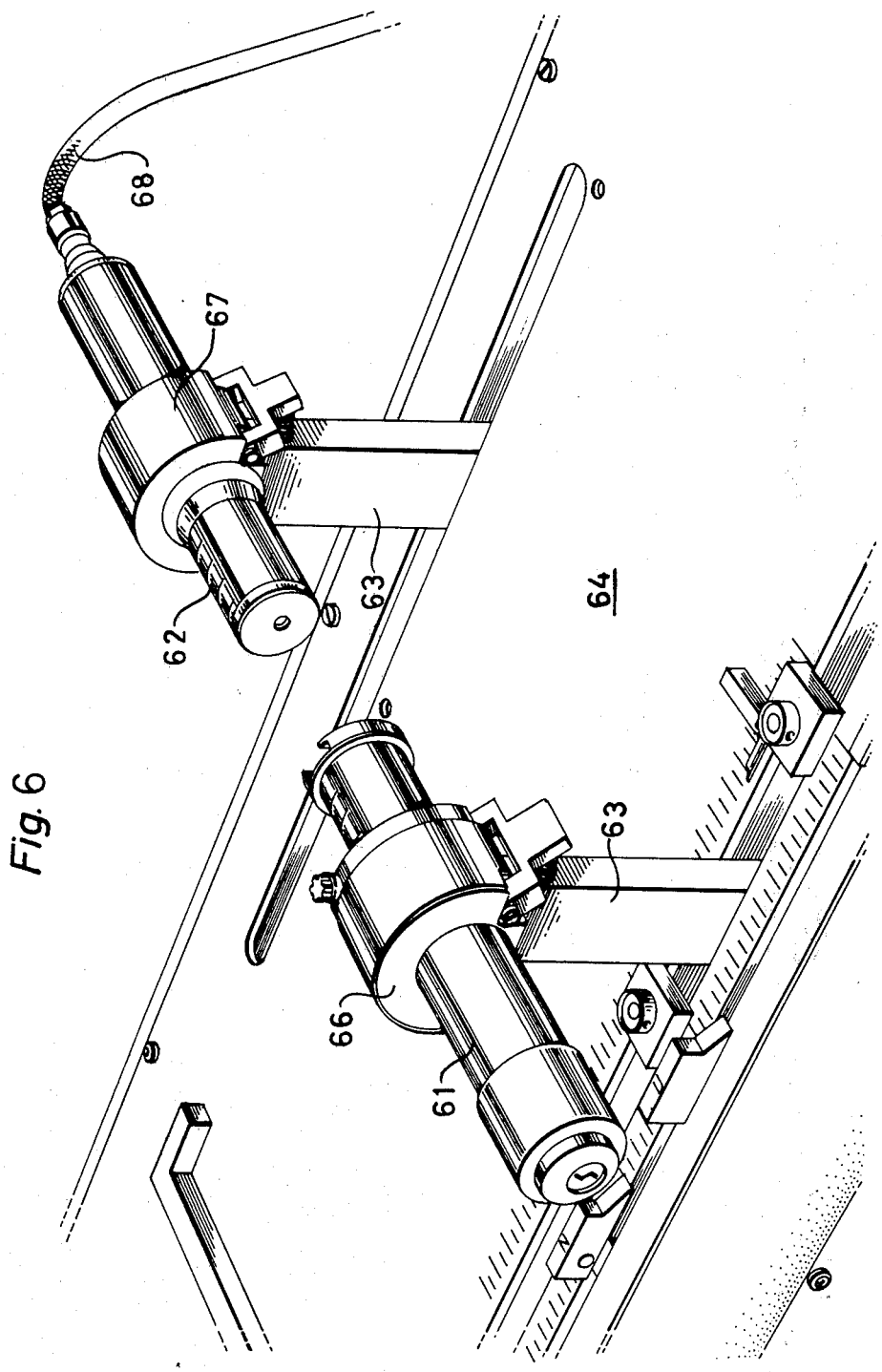

The preferred embodiment of the apparatus according to the invention illustrated in FIG. 3 comprises a radioactive radiation source 12 and a radiation detector 13, which are arranged on a displaceable fork 14, cf. also FIG. 6, such that the radiation can be scanned across a sample placed between the radiation source and the detector. Radiation source 12 is provided with a collimator such that photons are emitted in a narrow beam towards the detector 13. The detector produces a pulse for each incident photon, the amplitude of the pulse being proportional to the energy of the photon. The pulses from the detector are amplified in a pulse amplifier 15 and thereafter applied to two window discriminators 16 and 17. Said discriminators are arranged to pass well-defined pulses corresponding to a first and a second photon energy, respectively, to a logarithmic pulse frequency meter or ratemeter 18 and 19, respectively. The ratemeters produce a DC voltage proportional to the logarithm of the frequency of the input pulses. Each of the ratemeters 18 and 19 is connected to a conventional operational amplifier 22 and 23, respectively, via an adjustable reference level generator 20 and 21, respectively. These reference level generators make it possible to add constant DC voltages to the DC voltages obtained from ratemeters 18 and 19, such that the input voltages of amplifiers 22 and 23 are null when the photon beam from the radiation source passes directly through the air to the detector.

Amplifiers 22 and 23 are coupled to produce output signals having different polarities. The amplification of amplifier 22 can be varied by means of the adjustable feed-back resistor R1, while the amplification of amplifier 23 is constant. The outputs of amplifiers 22 and 23 are connected to a corresponding input resistor R2 and R3, respectively, of an operational amplifier 24 coupled as a summator. The amplification of amplifier 24 can be adjusted by means of an adjustable resistor R4. The DC voltage on the output of amplifier 24 will thus be proportional to the difference between the amplified input voltages of amplifiers 22 and 23.

The output of amplifier 24 can be connected via a switch 25 to a recording unit including a plotter 26, to a circuit 27 for zero setting control, and to an integrating circuit including a voltage-frequency converter 28, a threshold circuit 29, and and-gate 30, a scaler circuit 31, and a circuit 33 for digital display of the count of the scaler circuit, said circuit 33 being connected to the scaler circuit via a latch circuit 32.

Threshold circuit 29 is arranged to produce an output signal during a scanning operation, which enables and-gate 30 and starts the integration when the input signal to the threshold circuit, that is the output signal of amplifier 24, in a predetermined direction exceeds zero voltage by a predetermined value and which disables said and-gate and stops the integration when the input signal returns to zero voltage. The predetermined value is chosen such that noise on the output of amplifier 24 — inter alia due to the statistical fluctuations of the photon beam — cannot be expected to start the integration procedure.

Circuit 27, which by means of switch 25 can be connected to the outputs of reference level generators 20 and 21 to control that zero voltages are obtained when the radiation from the radiation source 12 falls directly on detector 13, includes an operational amplifier 34 and an indicating instrument 35. The time constant and the amplification of amplifier 34 have been increased in a narrow band around zero voltage by means of a feed-back circuit 36.

All units and circuits used in the apparatus according to FIG. 3 are well known to those skilled in the art, for this reason a more detailed description thereof should not be necessary. However, as to the logarithmic ratemeters, these suitably are of the diode pump pulse rate to direct current converter type.

When using the apparatus according to FIG. 3, first of all, reference level generators 20 and 21 are set, while directly irradiating detector 13, such that the input signals to amplifiers 22 and 23 are zero. The zero setting is controlled by connecting circuit 27 by means of switch 25 by turn to the outputs of the reference level generators. Thereafter, a sample of the substance, the influence of which is to be eliminated, for instance soft tissue, is inserted in the photon beam from the radiation source in the form of a dummy (for instance water) or a certain part of the object to be examined and resistor R1 is set such that the output voltage of amplifier 24 is zero, switch 25 then being in the position shown in FIG. 3. Finally the total scale factor of the apparatus is set by means of the adjustable resistor R4. This is suitably accomplished by inserting a phantom having a known content of the substance to be examined, for instance bone tissue, in the photon beam while adjusting resistor R4 until instrument 35 gives a correct reading, or alternatively until the integrating circuit upon scanning across the phantom shows a correct value on unit 33.

When the apparatus thus has been normalized or calibrated, the object to be examined is inserted between radiation source 12 and detector 13 and the photon beam is scanned across the object. The output voltage of amplifier 24 is then zero until the photon beam starts to pass through the part of the object containing the substance which is the subject of the examination. When the output voltage due to the absorption of radiation in the substance has increased to the level determined by the setting of threshold unit 29, and-gate 30 is enabled. Scaler unit 31 now starts to count, that is to integrate, the number of pulses transmitted from voltage-frequency converter 28 via the and-gate, the output frequency of the converter being proportional to the output voltage of amplifier 24. This procedure continues until the photon beam no longer passes through the part of the object which contains the substance subject to examination, that is, until the output voltage of amplifier 24 is again zero and threshold unit 29 disables and-gate 30. The count of scaler unit 31 can now be displayed digitally on unit 33 via latch circuit 32, the count being a direct measure of the content of said substance. The function of latch circuit 32 is to prevent that the count displayed is influenced by any new immediately following integration.

Figure 5B:
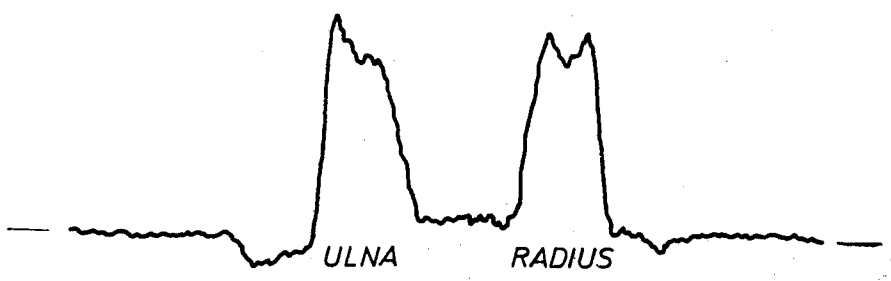
Figure 5C:
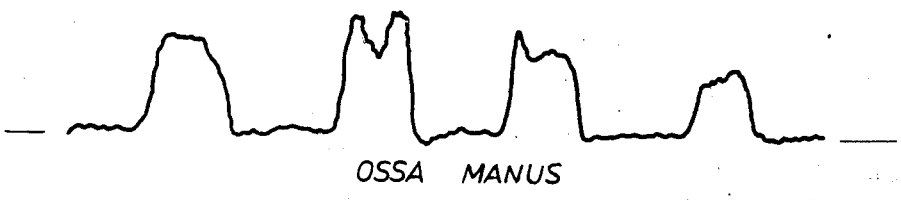

As is shown in FIG. 3, the output signal from amplifier 24 can be recorded by a plotter 26 during a scanning procedure, whereby a visual inpression of the distribution of a substance in a sample can be obtained. In FIG. 4 and 5, there are shown for the purpose of exemplification registrations obtained by an apparatus according to FIG. 3. FIG. 4A shows the output voltage of amplifier 24 when scanning a soft tissue phantom in the form of a cylindrical plastic vessel filled with water. FIG. 4B shows the output voltage of a new scanning procedure after the immersion of a bone tissue phantom in the form of an alumimium tube in the water in the plastic vessel. FIG. 4C shows the output voltage of yet another scanning of the aluminium tube immersed in the water but with one isotope channel (discriminator, pulse counter and reference level generator) disabled. FIG. 5A, B, and C show the output voltages from amplifier 24 when scanning human leg, arm and fingers, respectively. The "negative" parts of the registrations indicate the existance of fat tissue.

In FIG. 6 is shown an example of an arrangement for scanning the radioactive radiation across a sample (not shown). A radioactive radiation source 61 and a detector 62 are arranged on one each of the legs of a fork 63 suspended in a frame construction 64. Said frame construction comprises means for displacing fork 63 in accordance with a programmable scanning pattern. Both radiation source 61 and detector 62 are axially displaceable in a bracket 66 and 67, respectively, arranged on the corresponding fork leg. Detector 62 is connected to a pulse amplifier (not shown) via a cable 8.

When using the arrangement of FIG. 6 the part of a body to be examined is placed between source 61 and detector 62, after which the source and the detector are adjusted such that suitable distances between the source and the part of the body and between the part of the body and the detector, respectively, are obtained. Thereafter a programmed scanning operation can be made.

Although the present invention is particularly suitable for bone density measurements, it is obvious that it can be used in other connections while giving great advantages. Thus, other medical applications are conceivable where there is a desire to emphasize a certain type of tissue. Furthermore, the visual registration according to the invention means that very small structural changes are seen in a diagram. In other words an increase of the contrast is obtained, which is evident from a comparison between FIG. 4B and FIG. 4C.

What I claim is:

1. A method of examining a sample of biological tissue, which sample includes at least two different substances, by measuring the absorption of electromagnetic radiation, the method comprising the step of: transmitting electromagnetic radiation including photons of at least two different energies through the sample; simultaneously determining, for each of two predetermined photon energies, the logarithm of the radiation intensity of the radiation passed through the sample; processing the logarithmic values obtained so that the ratio of said values is changed by a predetermined factor substantially equal to the ratio between the mass absorption coefficient of one of said substances at the second photon energy and the mass absorption coefficient of said one substance at the first photon energy; and subtracting the logarithmic values thus processed from each other in order to obtain a simultaneous value so that the influence of said one substance on the magnitude of the examination value is eliminated.

2. A method according to claim 1, wherein the sample is scanned by sweeping the radiation across the sample in a first direction while continuously and simultaneously producing said examination value.

3. A method according to claim 2, further including integrating, during the scanning, the portion of the examination value produced which is a function of the influence of said other substance on the radiation, and obtaining a value which is proportional to the content of the sample of said other substance in terms of weight per length unit in a direction perpendicular to said first direction.

4. A method according to claim 2, further including the step of visually recording said examination value.

5. An apparatus for examining a sample of biological tissue, which includes at least two different substances, comprising: a radiation source emitting electromagnetic radiation having photons of at least two different energies; detector means for determining the intensity of radiation transmitted from said radiation source and falling on the detector means, said detector means being arranged to simultaneously produce a first signal having a value proportional to the logarithm of the radiation intensity at a first photon energy and a second signal having a value proportional to the logarithm of the radiation intensity at a second photon energy; means for processing said first and second signal so that the ratio between said quantities is changed by a predetermined factor; and means to produce an output signal having a value proportional to the difference between said changed quantities of the processed signals, said processing means being arranged to change said ratio so that said value of the output signal is substantially independent of the radiation influence of one of said substances.

6. An apparatus according to claim 5, wherein said radiation source and said detector means are arranged such that the radiation can be swept across the sample while continuously producing the output signal.

7. An apparatus according to claim 6, further including integrating means for integrating a value proportional to said value of the output signal.

8. An apparatus according to claim 5, wherein said detector means include a photon detector producing a pulse for each incident photon, the amplitude of said pulse being dependent on the energy of the photon; a first discriminator arranged to pass pulses corresponding to photons of said first energy level to a first logarithmic ratemeter; and a second discriminator arranged to pass pulses corresponding to photons of said second energy level to a second logarithmic ratemeter.

9. An apparatus according to claim 8, wherein said logarithmic ratemeters are arranged to produce a DC voltage, the amplitude of which is proportional to the logarithm of the pulse rate.

10. An apparatus according to claim 9, wherein each of said ratemeters is connected to a DC amplifier, the amplification factors of said DC amplifiers differing from each other by said predetermined factor, and wherein said DC amplifiers are connected to a summing means such that the amplified DC voltages of the ratemeters are subtracted from each other.

11. An apparatus according to claim 10, wherein each ratemeter is connected to its amplifier via a circuit for adding a reference signal such that the input voltage to the amplifier is zero when the radiation from the radiation source falls directly on the detector without passing through the sample.

12. An apparatus according to claim 10, wherein said summing means are connected to a counter via a voltage-frequency converter.

13. An apparatus according to claim 6, further including recording means for recording the magnitude of said value of the output signal.

14. An apparatus according to claim 5, wherein said radiation source includes a mixture of two isotopes.

15. An apparatus according to claim 14, wherein said two isotopes are I 125 and Am 241.

16. An apparatus according to claim 5, wherein said radiation source includes an isotope emitting photons of at least two different energies.

17. An apparatus according to claim 16, wherein said isotope is Xe 133.

18. An apparatus according to claim 5, wherein said radiation source is an x-ray tube, said detector means including window discriminators adapted to function at said first and second photon energies.

* * * * *